United States Patent [19]

Klippert et al.

[11] Patent Number: 4,903,794

[45] Date of Patent: Feb. 27, 1990

[54] ACOUSTICAL AMPLIFYING STETHOSCOPE

[76] Inventors: Don H. Klippert; Don E. Klippert, both of P.O. Box 3868, Napa, Calif. 94558

[21] Appl. No.: 171,956

[22] Filed: Mar. 23, 1988

[51] Int. Cl.[4] .......................... A61B 7/02; H04R 25/00
[52] U.S. Cl. ...................................... 181/131; 181/137; 181/160
[58] Field of Search ................. 181/131, 137, 159, 160

[56] References Cited

U.S. PATENT DOCUMENTS

| | | | |
|---|---|---|---|
| 705,934 | 7/1902 | Knudson et al. | 181/137 |
| 1,350,767 | 8/1920 | Aschburner | 181/137 |
| 1,445,711 | 2/1923 | Rayder | 181/137 |
| 1,657,078 | 1/1928 | Frederick et al. | 181/131 |
| 3,020,971 | 2/1962 | Cefaly | 181/137 |
| 4,270,627 | 6/1981 | Hill | 181/137 X |

*Primary Examiner*—Benjamin R. Fuller
*Attorney, Agent, or Firm*—Limbach, Limbach & Sutton

[57] ABSTRACT

A stethoscope for auscultating sounds from a subject, the stethoscope including a housing, a curvilinear convex diaphragm supported on the housing for interfacing with the site being auscultated and for receiving sounds therefrom, an enclosed acoustic chamber supporting on the housing and communicating with the curvilinear convex diaphragm for enhancing the fidelity of the received sounds, and means for transmitting the enhanced received sounds to the user, which can be a dual lumen wave guide to binaurals or a single lumen wave guide to one aural tube. With such an arrangement, the user is capable of taking vital signs through clothing, bandages, blankets are other obstructions, even in the presence of high ambient noise, and can auscultate low frequency sounds associated with heart sounds and bowel sounds with significantly improved clarity and volume.

31 Claims, 5 Drawing Sheets

U.S. Patent  Feb. 27, 1990  Sheet 1 of 5  4,903,794
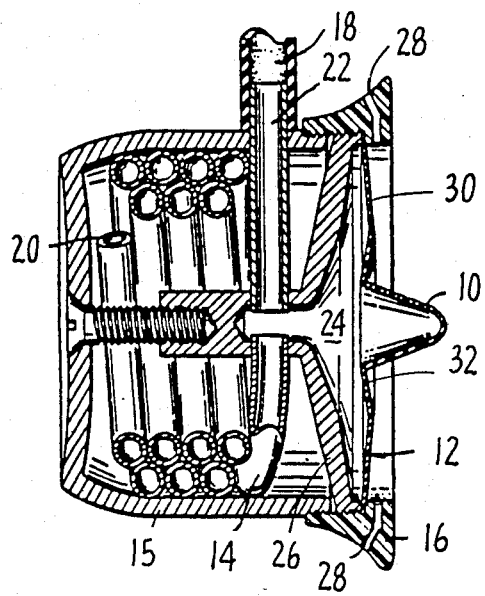
(PRIOR ART)
FIG. 1.
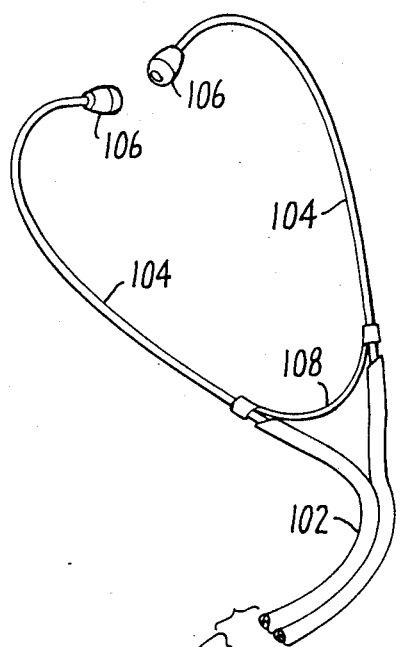
FIG. 3.
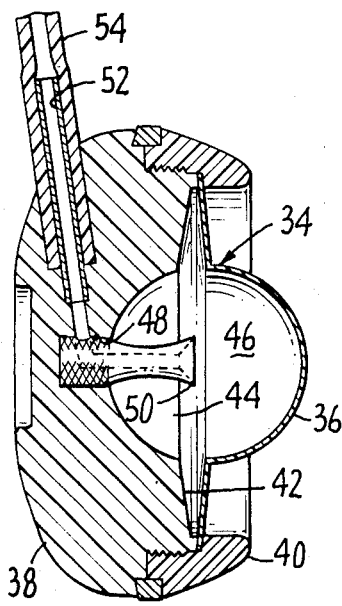
(PRIOR ART)
FIG. 2
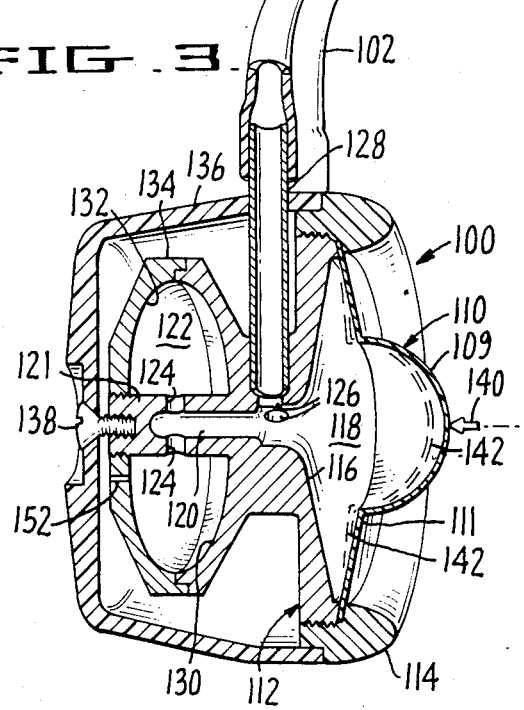

PARABOLIC

SPHERICAL

HYPERBOLIC

TRAPEZOIDAL

MODIFIED
TRAPEZOIDAL

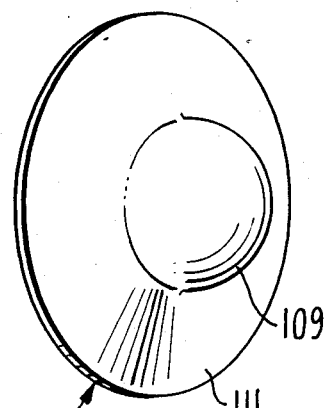
HEMISPHERICAL
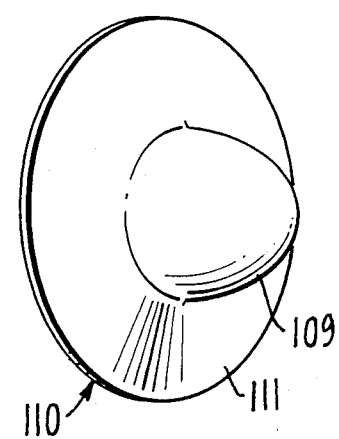
ELLIPSE, RATIO = 1.414
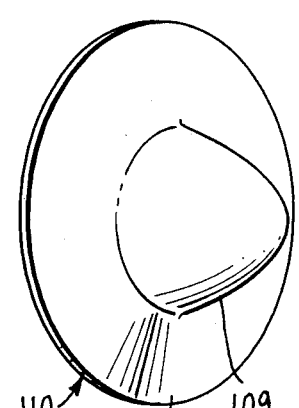
PARABOLIC
FIG.8A  FIG.8B  FIG.8C
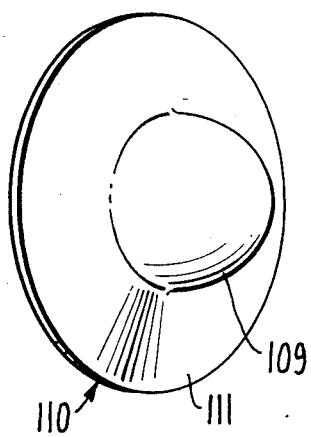
ELLIPSE, RATIO = 1.133
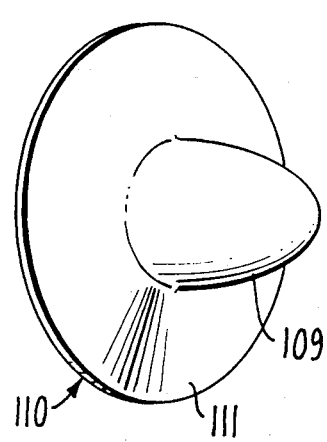
ELLIPSE, RATIO = 1.96
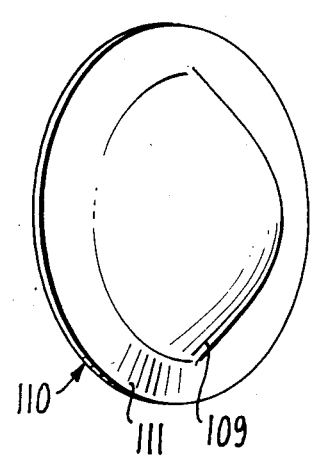
HYPERBOLIC
FIG.8D  FIG.8E  FIG.8F

ACOUSTICAL AMPLIFYING STETHOSCOPE

FIELD OF THE INVENTION:

This invention relates to the field of acoustical listening devices. More particularly, this invention relates to stethoscopes having a resonating chamber for improved sound pick-up and transmission.

BACKGROUND OF THE INVENTION:

The primary function of the medical stethoscope is to accurately transmit vital signs sounds from a human being or animal. To assess these sounds the medical practitioner auscultates his/her patient and listens to diagnose heart sounds, breath sounds, lung sounds and bowel sounds.

While auscultating the patient, the practitioner forms a mental image of the sounds based on the tone, pitch, amplitude, intensity and sound quality of the incoming sound signal. By comparing this image with what the practitioner regards as "normal" sounds, such information about the patient's heart condition, blood pressure, respiration, bowel sounds etc. can be used to assess the patient's physical condition.

If the sound signal provided by the stethoscope is lacking in frequency range, intensity, or clarity, the practitioner will be limited by insufficient diagnostic information to construct an accurate assessment of the patient's condition. Likewise, if the delivered signal through his/her stethoscope is attenuated or distorted, a correct diagnosis is very difficult. Thus, it is important that the sound transmission be accurate.

Traditional stethoscopes include a flat circular diaphragm for application to the surface of the body part. The diaphragm is connected to a housing to which a first end of a listening tube is attached. The second end of the listening tube is placed into the medical practitioner's ears, usually with ear pieces.

Problems with traditional stethoscopes include: (a) most existing stethoscopes do not faithfully reproduce all human organ sound functions, or vital sounds; (b) low frequency sounds (below 80 Hz) are not transduced or are difficult to recognize; (c) the tone quality of the signal produced is flat and lacks needed brilliance and character; (d) a usable signal cannot be produced if clothing separates the instrument from bare skin; and (e) signal strength is insufficient to monitor patients in ambulances, aircraft or boats, due to high level background noise.

As to problems (a) through (c), since 1940 and earlier, stethoscope designs have been inherently simplistic, and attenuate, or even block transmission of medium-frequency and low-frequency (20 to 60 Hz) sound waves emitted from the heart, lungs, muscles and lower bowels. These lower frequency sound waves are common to heart activity, both normal and pathological, and to certain lung sounds. Lung sounds include, for example, rhonchi, which are described as continuous, sonorous, low-pitched sounds, associated with acute or chronic bronchitis.

An improved stethoscope design is described in U.S. Pat. No. 4,270,627 to Hill which includes a probe pick-up diaphragm head, elongate resonating tubes, a perforated circular outer flange, and a tube for connecting the device to conventional ear pieces. The disclosed structure, such as that of FIG. 8 of the patent, provides greater-volume, low-frequency sounds, but does not deliver the higher frequency vital signs practitioners are accustomed to hearing from conventional stethoscopes. And further, the low frequencies originating within the heart are distorted and sound boomy by this design, and are believed to produce muting of important diagnostic high frequencies, such as systolic and diastolic murmurs and pericardial rub which occur in the frequency range of 120 through 660 Hz. Lung sounds and breath-sounds, as a class, have a proportionately smaller amount of low frequency components than heart sounds. Abnormal lung sounds termed "rales" and "ronchi" contain a variety of higher-pitch sounds. These sounds are also muted in the Hill design.

The inventors of the subject invention modified the design disclosed in Hill to incorporate a second transmission channel between the device and the ear pieces, shortened the resonating tube, and developed a "one-piece" hemispherical polycarbonate diaphragm in place of the probe pick-up diaphragm head. These changes produced a significant improvement over the Hill design, in terms of balancing the delivery of low to high frequencies emitted by the human heart. This modified design has been successfully marketed under the trademark CARDIOSONIC ACOUSTIC AMPLIFIER Model C-2000, by Biosources International, Inc., Napa, Calif..

A significant drawback of the Hill design is the cost to manufacture the labor intensive coiled tube "pick-up head." More specifically, these designs contemplate the step-drilling of a number of precision holes in a base; cutting and fitting of rigid tubes to engage the flexible transmission tubing (dual lumen); the cutting, pre-bending and wrapping the elongate resonant tube; soft-soldering the elongate resonant tube into the step-drilled holes in the base; the drilling, then plugging of passageway-connecting holes in the base; and constant quality control inspections to ensure open sound passageways. Further, in order to minimize the physical size of the finished stethoscope, the elongate resonant tubing must be precision wrapped just one way.

Subsequent to the Model C-2000, the inventors of the subject invention developed a more manufacturable stethoscope design designated the KLIPPERT RESONATOR, Model KR700. This design features a one-piece, hemispherical diaphragm, like the Model C-2000, but adds a hemispherical cavity in the housing of the stethoscope, complementary to the hemispherical diaphragm, so that the two hemispheres combine to form a spherical, resonant chamber. Also included is a horn-shaped collector, positioned at a focal point in the spherical, resonant chamber to collect sound from the chamber for routing to the transmission tubing. While the KR-700 design exhibits certain improved performance over the Hill device and C-2000 design, and most certainly over traditional devices, there is room for improving the fidelity of the sounds produced.

The problems of lack of amplification, limited frequency response range, poor tone quality, and painful ear seals of existing medical stethoscopes also apply to stethoscopes employed by mechanics and engineers. These stethoscopes are used in assessing machinery operation, particularly for troubleshooting and repairing potential equipment problems.

SUMMARY OF THE INVENTION:

The above and other problems and disadvantages of previous stethoscope designs are overcome by the present invention which includes a housing, a convex, curvilinear diaphragm supported on the housing for interfacing with the site being auscultated and for receiving sounds therefrom, an enclosed acoustic chamber supported on the housing and communicating with the curvilinear convex diaphragm for enhancing the fidelity of the received sounds, and means for transmitting the enhanced received sounds to the user.

It is therefore an object of the present invention to provide a stethoscope having an enclosed acoustic chamber for enhancing the sound received from a subject being auscultated.

It is another object of the present invention to provide a stethoscope which provides improved sound signal levels as well as improved sound fidelity.

It is a further object of the present invention to provide a stethoscope which includes an enclosed acoustical chamber positioned on a housing for enhancing sounds received from a subject being auscultated by way of a convex, curvilinear diaphragm interface.

It is still another object of the present invention to provide a stethoscope which is easily manufactured.

It is a still further object of the present invention to provide a stethoscope having a convex, curvilinear diaphragm interface which is biased to optimize soundwave compliance when pressed against the subject being auscultated.

It is another object of the present invention to provide a stethoscope which includes a solid sound shield for excluding extraneous ambient sounds.

These and other objectives, features and advantages of the present invention will be more readily understood upon consideration of the following detailed description and accompanying drawings.

BRIEF DESCRIPTION OF THE DRAWINGS:

FIG. 1 is a reproduction of FIG. 8 of U.S. Pat. No. 4,270,627, but with different reference numerals.

FIG. 2 is a cross section of the inventor's prior stethoscope design, Model KR700.

FIG. 3 shows a cross section drawing of the preferred embodiment of the present invention.

FIGS. 8A through 8F illustrate convex, curvilinear diaphragms in accordance with the present invention which embody a variety of different shapes.

Similar elements in each of the figures will be referred to by the same identifying numerals.

Figure 4A:
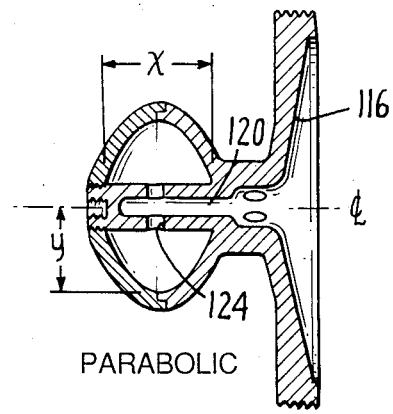
FIGS. 4A through 4B illustrate alternate acoustic chamber shapes in accordance with the present invention.

DETAILED DESCRIPTION OF THE PREFERRED EMBODIMENT:

FIG. 1 shows the stethoscope design described in U.S. Pat. No. 4,270,627 to Hill, FIG. 8, which includes a probe 10 attached to a diaphragm 12, a coiled resonating tube 14 positioned in a pick-up case 15, a perforated circular outer flange 16, and a tube 18 for connecting the device to conventional ear pieces (not shown). A cavity 24 is formed between probe 10, diaphragm 12, and base 26. The coiled resonating tube 14 opens at one end to cavity 24, and opens at its opposite end 20 where it vents to the atmosphere into pick-up case 15. Rigid tube 22 communicates sounds from cavity 24 to tube 18. Air vents 28 are provided to prevent a vacuum from forming between the skin of a patient and the diaphragm 12 when the pick-up head is in use.

It has been discovered that the vacuum relief vents 28 provide a path for high frequency sounds when the device is used in environments of high ambient noise, such as at accident sites, thus, degrading the performance of the device.

In the patent to Hill, probe 10 is described as being as sharp as possible to cause the probe contact to be as small a point as possible so that the sound waves at that single point are detected. The patent describes the large area sound pick-ups commonly used in other stethoscopes as having a disadvantage of integrating the sound over the many points covered. It has been found, contrary to the teachings of Hill, that it is desirable to have a patient interface which produces increased contact area over the Hill design, and which promotes sound-wave transfer wherever it is in contact with the site being auscultated.

In the patent to Hill, diaphragm 12 is described as having maximum flexibility at its outer annular ring 30, and less flexibility at its inner circular portion 32, to which probe 10 is attached. It is believed that this configuration results in mechanical dampening of the acoustical compliance of the diaphragm 12 and a resultant attenuation of sound signals being presented to diaphragm 12 of the device. And, testing has demonstrated that the geometry of Hill's diaphragm can produce a loud "snap" when the probe 10 is pressed against the subject being auscultated. It has been observed that the "secondary angle" formed between the outer annular ring 30 and the circular portion 32 acts as a toggle mechanism. When the contact force reaches certain critical loading, this triggers the toggle over center producing an undesirable acoustical "snap" during auscultation.

INVENTORS' DESIGN: MODEL C-2000

The stethoscope design Model C-2000, developed by the inventors of the subject application, modifies the Hill design in several respects, including the use of a hemispherical, convex diaphragm in place of the probe 10 and diaphragm 12 structure. This hemispherical, convex diaphragm is also used in the stethoscope design Model KR700, shown in FIG. 2, and bears reference designation 34.

Convex hemispherical diaphragm 34 is of one-piece construction and formed of thin, high-strength plastic, such as polycarbonate.

The central convex portion 36 provides an inherent rigidity for optimum strength in compressing clothing and/or soft-tissue. The central convex portion 36 affords mechanical loading of the patient's garments and subcutaneous tissue to produce a dense sound transmission corridor between the convex hemispherical diaphragm 34 and the sound source.

The physically thin nature of the convex hemispherical diaphragm 34 provides an acoustically transparent patient interface which is contact-sensitive, or pressure-sensitive for higher and lower frequency transmission. More specifically, extremely light forces, on the order of 0.3 to 0.8 ounces, release high-frequency sound waves into the device. Increased force, on the order of 2.0 to 8.0 ounces, buries the hemispherical patient interface further into the listening site to release high-fidelity, low-frequencies of heart sounds, bowel sounds, and/or carotid pulse activity. INVENTORS' DESIGN: MODEL KR700

FIG. 2 provides further detail of the inventors' prior stethoscope design Model KR700. The convex, hemispherical diaphragm 34 is supported on a base 38 and clamped to the base 38 by sound shield clamping ring 40. Base 38 has a face 42 in which is formed a concave, hemispherical cavity 44 complementary to the convex hemispherical diaphragm 34. Together, the convex, hemispherical diaphragm 34 and concave, hemispherical cavity 44 form a spherical acoustical chamber 46.

Positioned within spherical acoustical chamber 46 is a sound collecting horn 48. As can be seen from FIG. 2, the sound collecting end 50 of horn 48 is positioned at the center of the spherical acoustical chamber 46. The sound collecting end 50 has a 0.25 inch diameter opening which tapers at a 60 degree interior angle to a 0.125 inch diameter passage. A rigid tube 52 couples the collected sound from horn 48 to a single lumen wave guide 54.

THE PRESENT INVENTION

The preferred embodiment of the stethoscope of the present invention is shown in FIG. 3. Included are a transducer portion 100 which is coupled through dual lumen flexible sound-wave guides 102 and binaural tubes 104 to a pair of ear seals 106. The binaural tubes are biased apart by binaural spring 108.

Transducer 100 includes a convex, curvilinear diaphragm 110, which is clamped to a body 112 by threaded transducer sound shield 114. Body 112 has a face 116 which opposes the convex, curvilinear diaphragm 110, so that the two form an interface chamber 118. Sound collected in the interface chamber 118 is transmitted by an axial connecting passage 120 to an enclosed acoustic chamber 122. As can be seen from FIG. 3, axial connecting passage 120 is formed in post 12 which transverses the acoustic chamber 122.

Face 116 initially slopes linearly from its outer perimeter toward its center, preferably at approximately five (5) degrees relative to the plane containing the outer perimeter of face 116. Thereafter, in the vicinity of its center, face 116 curves away on a true radius of 0.25 inches until it is parallel with the walls of axial connecting passage 120.

Acoustic chamber 122 is preferably positioned in tandem with the interface chamber 118 and coaxially with respect to axial connecting passage 120. A pair of ports 124 is positioned radially with respect to axial connecting passage 120, and preferably at the audio focal point of acoustic chamber 122, to permit communication between acoustic chamber 122 and axial connecting passage 120. A pair of exit ports 126 is positioned in the axial connecting passage 120 between the interface chamber 118 and ports 124. Exit ports 126 are coupled to the dual lumen sound-wave guides 102 by exit tubes 128.

Acoustic chamber 122 is preferably formed by mating structures having complementary concave surfaces so that the mated surfaces enclose a chamber of the desired three-dimensional shape. As shown in FIG. 3, one of the complementary concave surfaces 130 is formed in body 112, concentrically with axial connecting passage 120.

The other complementary concave surface 132 is formed in an end cap 134. Post 121 is threaded at its distal end so that end cap 134 can be screwed to it and thence into engagement with body 112 at its outer periphery.

Finally, cover 136 is provided to engage sound shield 114 about its periphery and surround the acoustic chamber 122. Cover 136 is secured to body 112 by way of a screw 138, threaded into a tapped hole in the distal end of post 121.

In use, the transducer 100 of the stethoscope of the present invention is placed against the site being monitored so that convex, curvilinear diaphragm 110 initially makes contact with the site at the point indicated by solid arrow 140 in FIG. 3. As the practitioner applies force to urge the transducer 100 toward the site being monitored, convex, curvilinear diaphragm 110 is compressed toward face 116, as indicated by dashed lines 142. It is to be noted that sound shield 114 provides a solid, circumferential wall surrounding the convex, curvilinear diaphragm 110. The height of this wall is designed such that the sound shield 114 acts as a stop to prevent compression of the convex, curvilinear diaphragm 110 beyond a predetermined point. As will be explained in further detail below, this predetermined point is selected so as to increase the compliance of the convex, curvilinear diaphragm 110, thus making it more responsive to the sounds being auscultated. Further, sound shield 114 operates to prevent invasion of external extraneous ambient noise that may be present from entering interface cavity 118.

The sounds being auscultated are transmitted through convex, curvilinear diaphragm 110, into interface chamber 118, and through connecting passage 120 and ports 124 into acoustic chamber 122. Acoustic chamber 122 is proportioned so that sound energy in the frequency range of 10 Hz to 800 Hz is sonically intensified and acoustically enhanced.

From another point of view, acoustic chamber 122 loads connecting passage 120 so that the signal strength of sounds in the range of 10 Hz to 800 Hz are enhanced.

The sound signals which are present in connecting passage 120 pass through exit ports 126, thence through exit tubes 128, and into dual lumen sound-wave guide 102 for transmission to the user.

The various components of the preferred embodiment of the present invention will now be described in greater detail.

ACOUSTICAL CHAMBER 122

Figure 4B:
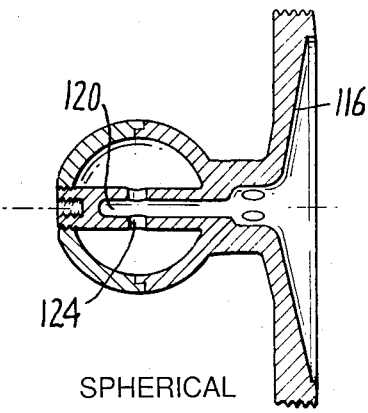
Figure 4C:
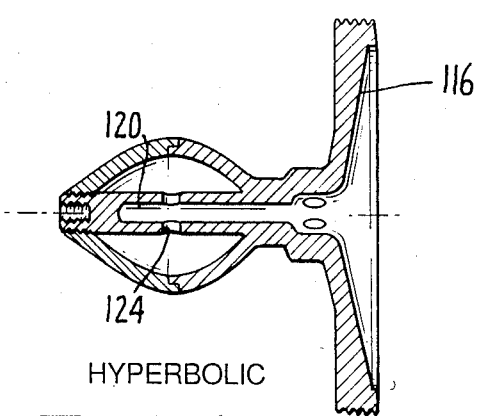
Figure 4D:
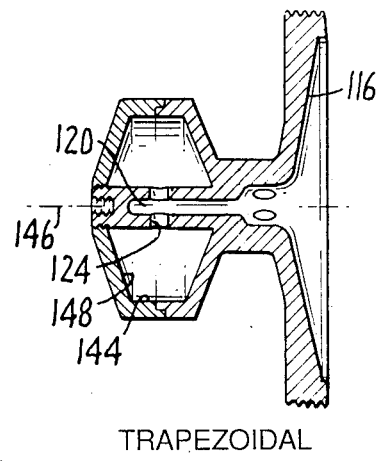
Figure 4E:
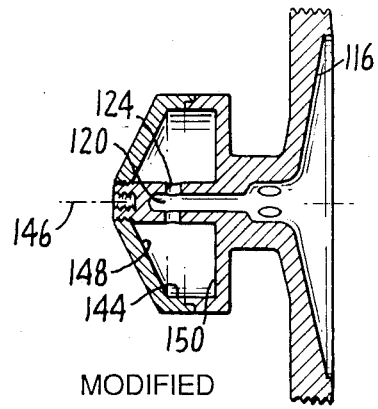

In accordance with the present invention, the acoustical chamber 122 is preferably shaped as an ellipsoid. FIGS. 4A through 4E illustrate the cross section of other shapes which are suitable for use in acoustical chamber 122. Chambers shaped according to the cross sections illustrated in these figures should be formed of constant radius about the center line/axis of the connecting passage 120. These include a parabolic cross section as shown in FIG. 4A to form a paraboloid, a hemispherical cross section as shown in FIG. 4B to form a spheroid, a hyperbolic cross section as shown in FIG. 4C to form a hyperboloid, a trapezoidal cross section as shown in FIG. 4D to form a trapezoid, and a modified trapezoidal cross section as shown in FIG. 4E.

For each acoustical chamber shape, it is preferred that the ratio, y/x, of its radius, y, to its axial dimension, x, be between a minimum of 1 to a maximum of 4.3. The radius, y, is defined as the distance from the center line of the connecting passage 120 to the outermost radial distance of the chamber. The axial dimension, x, is defined as the distance along the center line of the enclosed chamber. See FIG. 4A, for example.

In the preferred embodiment of the present invention shown in FIG. 3, the radial to axial ratio is substantially 0.625/0.4 or 1.56.

Within the range of acoustical chamber dimensions described above, various vital sign frequencies can be enhanced, or amplified, by selecting the appropriate chamber volume. The shape of the chamber can also be selected to complement packaging requirements for the particular instrument being designed.

It is to be noted that while both the trapezoidal cross section of FIG. 4D and the modified trapezoidal cross section of FIG. 4E feature a surface 144 at their periphery which is parallel to the center line 146, and another surface 148 which extends outwardly at an angle from the center line to intersect with the parallel surface 144, the modified trapezoidal cross section has a surface 150 which extends outwardly at right angles from center line 146.

It is to be understood that while certain acoustical chamber shapes have been described, the use of other shapes which satisfy the volume and size factors discussed above are contemplated in accordance with the present invention.

VENTING THE ACOUSTICAL CHAMBER

It is also to be understood that, unlike the elongated, resonant tubing described in the patent to Hill referenced above, the present invention employs an acoustical chamber which is effectively "closed" to the sound frequencies of interest. Thus, when the practitioner inserts ear seals 106 into his or her ears, a closed acoustical system is formed. The inventors have found that optimum performance of a stethoscope is dependent upon positive air-tight seals at all junctions. In the absence of such air-tight seals, sound intensity will fall off markedly.

However, the inventors have discovered that when such closed systems are air-tight, an over-pressure can result in the practitioner's ears when the transducer 100 is pressed against the site being auscultated. Over-pressure of the ear-drum upsets the delicate hearing mechanism within the human ear and accurate assessment of sounds becomes difficult. Such over-pressure is developed when the column of air behind the diaphragm, in the interface chamber 118 and in the acoustical chamber 122, is compressed due to axial movement of the convex, curvilinear diaphragm 110.

It has been found that acoustical balance of optimum sound intensity, i.e. minimal over-pressure, can be achieved by venting the acoustical chamber 122 to the atmosphere. Preferably, a single vent hole is used having a diameter of between 0.010 and 0.015 inches. In FIG. 3, such a vent hole is indicated by reference numeral 152. With such a vent hole, equilibrium of the practitioner's ear drum is quickly accomplished but sound energy is not attenuated. In other words, a vent hole of the size described above is effectively "closed" to the sound wave frequencies of interest.

ORIENTATION OF THE ACOUSTICAL CHAMBER

In the preferred embodiment of the present invention, the acoustical chamber 122 is oriented axially tandem with the interface chamber 118. That is, the interface chamber 118 and the acoustical chamber 122 are spaced side by side and coaxial with respect to one another.

It is to be understood that the present invention also contemplates that the acoustical chamber can be positioned radially tandem, or angularly tandem with respect to the interface chamber 118. In a radially tandem configuration, the acoustical chamber 122 is positioned so that its axis is parallel to a radius of the interface chamber 118; i.e. at right angles to the axis or center line of interface chamber 118. In such configuration, connecting passage 120 would include a ninety degree turn.

In an angularly tandem configuration, the acoustical chamber 122 is positioned so that its axis will lie at an angle between zero and ninety degrees relative to the axis of interface chamber 118. In such a configuration, connecting passage 120 would include a bend substantially equal to the angle at which the axis of the acoustical chamber is oriented relative to that of the interface chamber 118.

Figure 7:
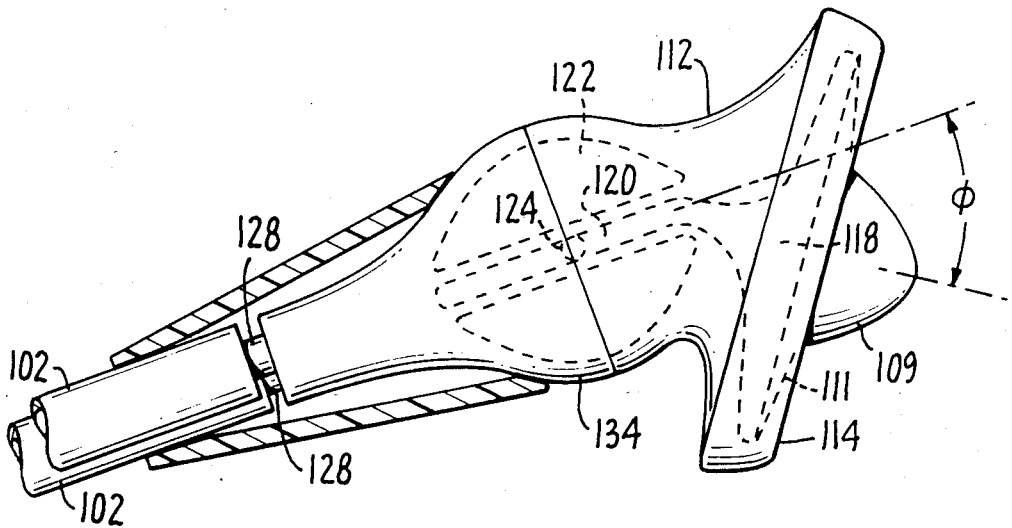
FIG. 7 is a cross sectional view of an angularly tandem arrangement of the acoustical chamber and interface chamber in accordance with the present invention.

FIG. 7 illustrates an angularly tandem configuration in which a hyperbolic-shaped acoustical chamber 122 is shown with the axis of connecting passage 120 at an angle $\phi$ with respect to the axis of interface chamber 118. Exit tubes 128 are preferably angled slightly to provide for passageway congruence at a point where they intersect port hole 124, or downstream therefrom. It is to be noted that in FIG. 7, the exit tubes 128 and dual lumen wave guides 102 are positioned "in-line" or "in-series" with the interface chamber 118 and the acoustical chamber 120 such that connecting passageway extends all the way through post 121 and into exit passage 128. While ports 124 are shown in post 121 to provide communication between connecting passageway and acoustical chamber 122, such communication can be provided by the use of a two piece post having ends which oppose each other at about the center of the acoustical chamber 122. A gap would be provided between the opposing ends.

This design lends itself conveniently for use in preventive maintenance on machinery and mechanical devices.

ACOUSTICAL PASSAGEWAYS IN THE TRANSDUCER

When sound paths are of insufficient size in metal parts, sound-wave energy can be attenuated or muted. However, in typical stethoscope applications, sound source energy is very small and large mass-flow of sound waves in the air-medium is absent. As such, sound passages or corridors can be quite small in diameter; e.g. 0.040 inches. In accordance with the present invention, the diameter of the various sound paths is preferably greater than 0.040 inches, and preferably in the range of 0.090 to 0.170 inches.

It is to be understood that the above sound path dimensions represent preferred minimum sizes, and that multiple pathways working together, each within the preferred range, can be used. For example, in the embodiment of FIG. 3, two ports 124 of 0.090 inches apiece are used to couple the axial connecting passage 120 to acoustical chamber 122. Four such ports can be used with satisfactory results.

In the embodiment of FIG. 3, axial connecting passage 120 is approximately 0.136 inches in diameter, and exit ports 126 are approximately 0.125 inches in diameter.

SOUND SHIELD 114

The sound shield 114 is similar to that used in the inventors' previous stethoscope models C-2000 and KR700. Sound shield 114 is constructed to provide a solid, heavy wall of material having a leading edge radiused to provide an air-tight seal at the listening site. Such construction permits the sealing out of extraneous ambient noise under extreme conditions normally adverse to patient/victim assessment. Preferably, sound shield 114 is constructed of high strength, durable compression molded or thermo-forming plastic material, which provides the added benefit of being a poor heat conductor so that it is "not cold" when placed on bare skin.

CONVEX, CURVILINEAR DIAPHRAGM 110

The convex, curvilinear diaphragm 110 shown in FIG. 3 has a hemispherical shape. It has been discovered that other curvilinear shapes can be used with satisfactory results. These shapes include parabolic, elliptical, and hyperbolic. The elliptical forms include thirty, forty-five and sixty degree elliptical shapes.

Preferably, the convex, curvilinear diaphragms of the present invention are formed from a sheet of polycarbonate material, having a thickness in the range of 0.006 to 0.012 inches. The sheet is thermal/vacuum formed over a precision mold having the particular curvilinear shape desired. In practice, the actual mold is formed by using a controlled radius, such as 0.5 inches, such that the shape has a diameter of 1.0 inch at the intersection of the curvilinear shape with the annular, nearly flat zone 111, FIG. 3, of the diaphragm. The convex portion, or protruding nose, of each shape should extend or retract in proportion to the radius used in forming the shape. Preferably, the protruding nose of each shape should protrude approximately 0.15 to 0.40 inches beyond the outer most portion of sound shield 114.

The mechanical molding of the convex, curvilinear diaphragm 110 into the above shapes serves to stiffen the material immensely such that it is very effective in compressing subcutaneous tissue, burn-bandages, clothing, blankets, animal hair, feathers, and even functions through wet-suits. When pressed against a subject being auscultated, the subcutaneous tissue and muscle tissue are substantially compressed by the convex, curvilinear diaphragm 110 with a resulting perceptive increase in the sound signal to the practitioner.

Preferably, the annular zone 111 is "nearly flat∞ but slightly biased toward the subject to produce a thrusting forward of the convex, curvilinear diaphragm 110. In the preferred embodiment of the present invention, clamping angles of the convex, curvilinear diaphragm 110, relative to the plane containing the perimeter of the diaphragm 110, are on the order of two (2) to four (4) degrees. As explained above, this mechanical biasing of the diaphragm 110 results in a reactance force being applied against the convex portion of the diaphragm when it is actually pressed against the site being auscultated. This neutralizes the tension of the convex, curvilinear diaphragm 110 and counteracts any "drum-head tension" across it so as to render it more acoustically compliant. This design feature greatly reduces the dampening or attenuating of sound signals through the interface provided by the convex, curvilinear diaphragm 110. Thus, the acoustical transfer-function of this diaphragm is optimized to permit the delivering of high-volume sound into the interface chamber 118.

Figure 5:
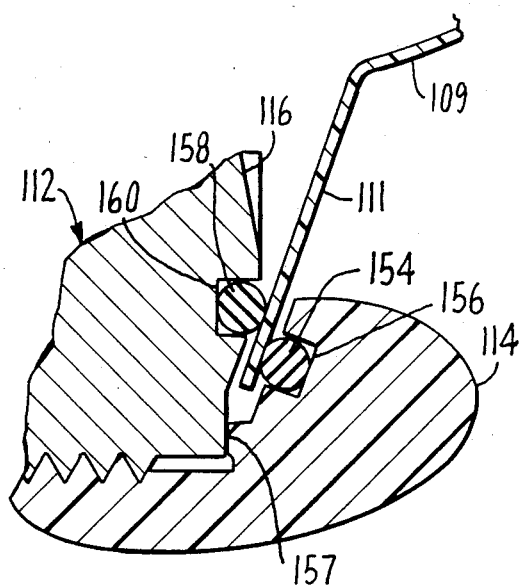
FIG. 5 is a sectional cross section illustrating one method of biasing the convex, curvilinear diaphragm of the present invention.

FIG. 5 illustrates one structure for biasing the convex, curvilinear diaphragm 110. An outer annular "O" ring 154 is positioned in a groove 156 that has been formed in sound shield 114. An inner annular "O" ring 158 is positioned in a groove 160 that has been formed in body 112. The annular flat portion 111 of convex, curvilinear diaphragm 110 is then clamped between "O" rings 154 and 156. Grooves 156 and 160 are positioned so that "O" ring 154 comes into contact with annular flat portion 111 closer to the perimeter of diaphragm 110 than the point of contact of "O" ring 156. "O" rings 154 and 156 can be of Teflon material.

Annular stop 157 is provided to operate in conjunction with grooves 156 and 160, and "O" rings 154 and 158, to prevent over loading of the diaphragm 110 beyond the point of optimum bias. Preferably when optimally biased, diaphragm 110 is in light contact with "O" rings 154 and 158, and out of contact with any of the other mechanical parts.

FIGS. 8A through 8F illustrate convex, curvilinear diaphragms in accordance with the present invention which embody a variety of different shapes. FIG. 8A illustrates a hemispherical convex portion 109. FIG. 8B illustrates an elliptical convex portion 109, having a major to minor axis ratio of approximately 1.414. This corresponds to a forty-five (45) degree ellipse. FIG. 8C illustrates a parabolic convex portion 109. FIG. 8D illustrates an elliptical convex portion 109, having a major to minor axis ratio of approximately 1.133. This corresponds to a sixty (60) degree ellipse. FIG. 8E illustrates an elliptical convex portion 109, having a major to minor axis ratio of approximately 1.96. This corresponds to a thirty (30) degree ellipse. FIG. 8F illustrates a hyperbolic convex portion 109. It is to be understood that the specific ellipse ratios and the radii shown in FIGS. 8A through 8F are intended to be illustrative and that other ratios and radii can be used within the scope of the present invention. Further, while the convex, curvilinear diaphragm has been illustrated in terms of spheroid, hyperboloid, ellipsoid, paraboloid, and trapezoidal volumes, other curvilinear volumes can be employed within the spirit of the present invention.

It has been found that the volume contained within the convex, curvilinear diaphragm 110 affects which frequencies are emphasized by the present invention. More specifically, the smaller the volume, the higher the perceived frequency. Therefore, where higher (lower) sounds are of greatest interest, a convex, curvilinear diaphragm having a small (large) volume is preferred. It has also been found that an increase in size of the convex, curvilinear diaphragms results in increased volume of sound, up to a point of optimum sound intensity for the particular design. In accordance with the present invention, a "system" of variable volume convex, curvilinear diaphragms can be assembled which offer transmission of perceptibly lower (or higher) frequency sound signals depending upon the specific application. Such a system also would be useful in monitoring rotating machinery in order to anticipate preventative maintenance.

ACOUSTICAL TRANSFER FUNCTION

Figure 9:
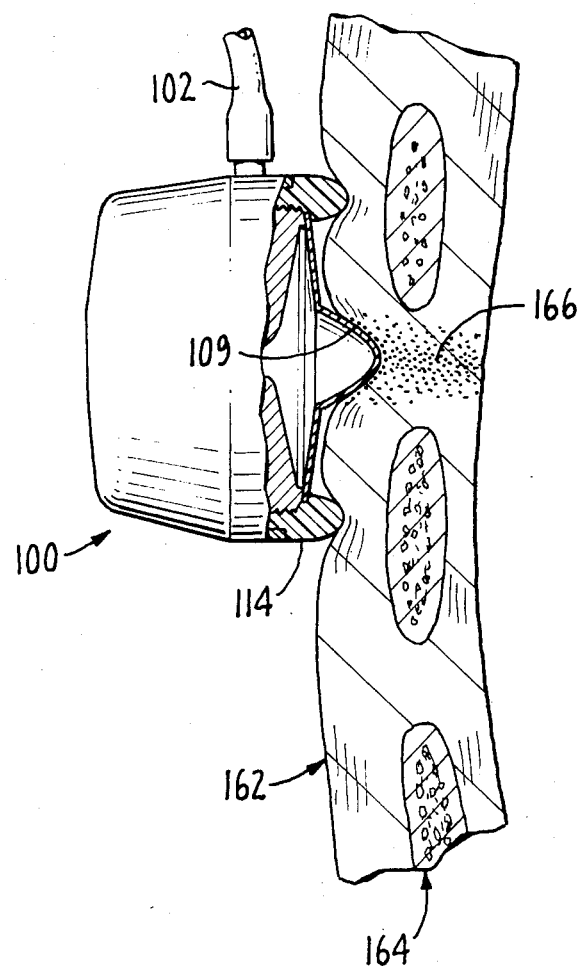
FIG. 9 illustrates the manner in which a sound transmission corridor is created by the stethoscope of the present invention when used on humans or animals.

The shape of the convex, curvilinear diaphragm 110 is believed to be an important component in acquiring the sound signal from the subject and transferring it into the transducer 100. FIG. 9 illustrates the manner in which the convex portion 109 of the convex, curvilinear diaphragm 110 compresses subcutaneous and muscle tissue 162 to produce a dense corridor 166 for soundwave transmission. FIG. 9 illustrates the present invention in use in the chest area of a human or animal. There, subcutaneous and muscle tissue 162 surround a rib cage 164. The present invention is placed in an area between the ribs, and is pressed against the chest until sound shield 114 comes into contact with the fleshy epidermis. It is believed that this causes a compaction of clothing and/or tissue to achieve an increased density and hence improved sound transmission qualities.

COVER 136

Cover 136 forms an outer envelope in conjunction with sound shield 114 that provides an aesthetically pleasing appearance to the stethoscope of the present invention, as well as provides protection to the transducer element. The envelope can be constructed from molded plastic, such as ABS plastic, formed metal, or a combination of both. Other materials include acetal resins and polycarbonate.

DUAL LUMEN WAVE GUIDE 102 AND EAR SEALS 106

Dual lumen wave guide 102 is preferably constructed to provide maximum exclusion of ambient noise. For example, tubing constructed of polyvinylchloride material, having a wall thickness of approximately 0.10 inches has been found to provide satisfactory results. Further, in the preferred embodiment of the present invention, the interior surface of the dual lumen wave guide 102 is made smooth to minimize acoustical attenuation through the wave guide 102. A dual, versus single, lumen wave guide is preferred because it has been found that the increased capacity of the dual wave guide passes more freely the higher frequency sounds from the transducer.

Ear seals 106 are preferably formed of a soft, molded silicone material so that a better acoustic seal is obtained between the practitioner's ears and the ear seals 106, and extended monitoring can be accomplished with greater comfort.

Figure 6:
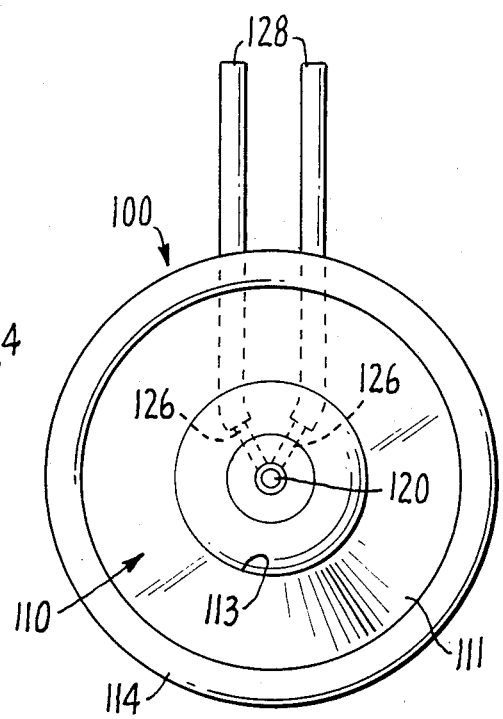
FIG. 6 is a plan view of the transducer portion of the present invention.

FIG. 6 is a front view of transducer 100 of the present invention illustrating the arrangement of the sound shield 114, convex, curvilinear diaphragm 110, exit tubes 128, exit ports 126, and axial connecting passage 120 relative to one another. As can be seen from the figure, the convex portion 109 of the convex, curvilinear diaphragm 110, is concentric with axial connecting passage 120. The point at which convex portion 109 joins flat portion 111 is indicated by reference numeral 113. It can also be seen that exit tubes 128 are preferably parallel to one another at a point removed from transducer 100, but that the tubes bend toward one another as they enter the body 112 of transducer 100.

In light of the above, it should be appreciated that the present invention represents a significant improvement over prior stethoscope designs. Not only are improved signal fidelity and volume achieved, but a significantly more manufacturable device is provided. The present invention can be produced by automatic screw machines, computer numerical control automatics, or die-casting such as with a zinc alloy, or aluminum for light weight.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

What is claimed is:

1. A stethoscope including a transducer communicating with ear seals by way of a lumen wave guide, for use in auscultating sounds from a subject, wherein the transducer comprises:
   a housing;
   means supported on one end of the housing for interfacing with the subject being auscultated to receive the sounds from the subject; and
   a separate enclosed acoustic chamber formed in an opposite end of the housing from the interfacing means and communicating with the lumen wave guide by way of a passageway which extends through the housing and connects the interfacing means to the enclosed acoustic chamber for enhancing the sounds received by the interfacing means.

2. The stethoscope according to claim 1 wherein said interfacing means include
   a convex, curvilinear diaphragm having an annular portion and a convex portion; and
   means for shielding a region around the convex, curvilinear diaphragm from external ambient sounds.

3. The stethoscope according to claim 2 wherein the convex portion of the diaphragm has an ellipsoidal shape.

4. The stethoscope of claim 2, wherein the convex portion of the diaphragm has a spheroid shape.

5. The stethoscope of claim 2, wherein the convex portion of the diaphragm has a paraboloid shape.

6. The stethoscope of claim 4, wherein the convex portion of the diaphragm has a forty five degree ellipsoidal shape.

7. The stethoscope of claim 4, wherein the convex portion has a sixty degree ellipsoidal shape.

8. The stethoscope of claim 2, wherein the diaphragm is formed of a thin plastic material.

9. The stethoscope of claim 8, wherein the diaphragm has a thickness of between 0.006 to 0.012 inches.

10. The stethoscope of claim 2, wherein the convex, curvilinear diaphragm forms an interface chamber with the housing, and the enclosed acoustical chamber is positioned axially tandem with respect to the interface chamber and diaphragm; and further wherein the interface chamber communicates with the enclosed acoustical chamber by way of an axial connecting passage.

11. The stethoscope of claim 10, wherein the enclosed acoustical chamber includes means for venting the enclosed acoustical chamber.

12. The stethoscope of claim 11, wherein the venting means do not alleviate energy of frequencies present in the sounds being auscultated.

13. The stethoscope of claim 12, wherein the venting means include a passage having a diameter between 0.010 and 0.015 inches.

14. The stethoscope of claim 1, wherein the enclosed acoustical chamber has an ellipsoidal shape.

15. The stethoscope of claim 1, wherein the enclosed acoustical chamber has a spheroidal shape.

16. The stethoscope of claim 1, wherein the enclosed acoustical chamber has a hyperboloid shape.

17. The stethoscope of claim 1, wherein the enclosed acoustical chamber has a trapezoidal shape.

18. The stethoscope of claim 1, wherein the enclosed acoustical chamber has a paraboloid shape.

19. The stethoscope of claim 1, wherein the enclosed acoustical chamber has a modified trapezoidal shape.

20. The stethoscope of claim 10, wherein the axial connecting passage includes
first port means for communicating between the axial connecting passage and the enclosed acoustical chamber;
second port means for communicating between the axial connecting passage and the lumen wave guide.

21. The stethoscope of claim 20, wherein the first port means are positioned at an audio focal point of the enclosed acoustical chamber.

22. The stethoscope of claim 20, wherein the first and second port means have diameters greater than 0.040 inches.

23. The stethoscope of claim 20, wherein the first and second port means have diameters between 0.090 to 0.120 inches.

24. The stethoscope of claim 2, wherein the means for shielding comprise a solid annular shaped structure, supported on the housing to be concentric with the convex, curvilinear diaphragm, further wherein a height of the solid annular shaped structure is selected so that the convex portion of the convex, curvilinear diaphragm protrudes a predetermined distance beyond the means for shielding.

25. The stethoscope of claim 2, wherein the annular portion of the convex, curvilinear diaphragm is biased outwardly with respect to a plane containing a perimeter of the convex, curvilinear diaphragm.

26. The stethoscope of claim 25, wherein the amount of biasing is between two to four degrees with respect to the plane containing the perimeter of the curvilinear diaphragm.

27. The stethoscope of claim 1, wherein the enclosed acoustical chamber has a radial cross section defined in terms of a center line, a radius "y," and an axial distance, "x," and further wherein a ratio of "y" to "x" is predetermined, where "y" is defined as the distance from the center line to an outer-most radial distance of the radial cross section, and "x" is defined as the distance along the center line of the radial cross section.

28. The stethoscope of claim 27, wherein the ratio of "y" to "x" is between 1 and 4.3.

29. The stethoscope of claim 2, wherein the convex portion of the convex, curvilinear diaphragm extends beyond the shielding means by a predetermined amount.

30. The stethoscope of claim 29, wherein the convex portion of the convex, curvilinear diaphragm extends beyond the shielding means by an amount in a range of 0.15 to 0.40 inches.

31. The stethoscope of claim 1, wherein the lumen wave guide is positioned in series with the enclosed acoustical chamber and the interfacing means.

* * * * *